United States Patent [19]

Moguilewsky et al.

[11] Patent Number: 5,084,472

[45] Date of Patent: Jan. 28, 1992

[54] APPLICATION OF 1-(3'-TRIFLUOROMETHYL-4'-NITRO-PHENYL)-4,4'-DIMETHYLIMIDAZOLINE 2,5-DIONE IN THE TREATMENT OF HORMONE-DEPENDENT CANCERS OTHER THAN THAT OF THE PROSTATE

[75] Inventors: Martine Moguilewsky; Marie M. Bouton, both of Paris, France

[73] Assignee: Roussel, Romainville, France

[21] Appl. No.: 529,948

[22] Filed: May 29, 1990

Related U.S. Application Data

[63] Continuation-in-part of Ser. No. 224,877, Jun. 17, 1988, abandoned.

[51] Int. Cl.$^5$ ............................................. A61K 31/415
[52] U.S. Cl. ...................................... 514/389; 514/391
[58] Field of Search ................................ 514/389, 391

[56] References Cited

U.S. PATENT DOCUMENTS 4,097,578  6/1978  Perronnet et al. .................. 514/389

OTHER PUBLICATIONS

Chemical Abstracts 91:1869572 (1979).

Primary Examiner—Jerome D. Goldberg
Attorney, Agent, or Firm—Bierman and Muserlian

[57] ABSTRACT

A method of treating hormone-dependent cancer of an organ selected from the group consisting of bladder, brain, breast, lymphatic systems, kidney, liver, skin and ovaries in warm-blooded animals having such a cancer comprising administering to said warm-blooded animals an amount of 1-(3-'trifluoromethyl-4'-nitro-phenyl)-4,4-dimethyl-imidazoline-2,5-dione sufficient to combat said hormone-dependent cancer.

3 Claims, No Drawings

APPLICATION OF 1-(3'-TRIFLUOROMETHYL-4'-NITROPHENYL)-4,4'-DIMETHYLIMIDAZOLINE 2,5-DIONE IN THE TREATMENT OF HORMONE-DEPENDENT CANCERS OTHER THAN THAT OF THE PROSTATE

PRIOR APPLICATION

This application is a continuation-in-part of U.S. patent application Ser. No. 224,877 filed June 17, 1988, now abandoned.

STATE OF THE ART 1-(3-'trifluoromethyl-4'-nitrophenyl)-4,4-dimethyl-imidazoline 2,5-dione of the formula

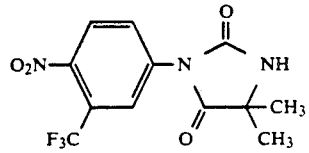

has been described in French Patent No. 2,329,276 published on May 27, 1977 as is the use of this product in the treatment of adenones and neoplasia of the prostate. There has subsequently been described in U.S. Pat. No. 2,465,486 and in numerous publications, the use of the combination of 1-(3'-trifluoromethyl-4'-nitrophenyl)-4,4-dimethylimidazoline and peptides of LH-RH type in the treatment of adenocarcinoma of the prostate and benign hypertrophy of the prostate, of endometriosis, of dysmenorrhea, hirsutism and hormone-dependent mammary tumors.

In addition, the presence of androgen receptors has been described in cancerous cells of some organs. For example, the following publications can be quoted:

bladder tumor: Urology 1985, Feb. Vol. 25(2), pp. 161 to 163;
brain tumor: J. Neurooncology 1983, Vol. 1(3), pp. 179 to 189;
breast tumor: Cancer 1984, Dec. 1, Vol. 54(11), p. 2436 to 2440;
lymphoma: J. Steroid Biochemistry, 1984, Oct., Vol. 21(4), pp. 421 to 426;
kidney tumor: Cancer 1984, Aug. 1, Vol. 54(3), pp. 477 to 481;
liver tumor: Br J. cancer 1983, Dec., Vol. 48(6), pp. 791 to 796;
melanoma: Br J. Dermatol. 1982, Nov., Vol. 107, suppl. 23, pp. a54 to 59;
ovary tumor: J. Endocrinol 1981, Sept. Vol. 90(3), pp. 421 to 431.

The previously quoted publication "Cancer 1984, Aug. 1, Vol. 54(3), pp. 477 to 481" describes the absence of the activity of Flutamide (2-methyl N-(4-nitro-3-(trifluoromethyl)-propanamide) in renal carcinoma. To the knowledge of applicants, the use of 1-(3- trifluoromethyl-4'-nitrophenyl)-4,4-dimethyl-imidazoline-2,5-dione in the treatment of hormone-dependent cancers other than that of the prostate has never been described.

A subject of the present patent application is therefore the use of 1-(3'-trifluoromethyl-4'-nitrophenyl)-4,4-dimethylimidazoline 2,5-dione in the treatment of hormone-dependent cancers other than that of the prostate in warm-blooded animals, including humans, as well as the use of 1-(3'-trifluoromethyl-4'-nitro-phenyl)-4,4'-dimethylimidazoline 2,5-dione for obtaining a medicament intended for the treatment of hormone-dependent cancers other than that of the prostate.

More particularly, a subject of the present patent application concerns the application of 1-(3'-trifluoromethyl-4'-nitrophenyl)-4,4-dimethylimidazoline 2,5-dione in the treatment of cancer affecting the following organs: bladder, brain, breast, lymphatic system, kidney, liver, skin and ovaries, as well as the use of 1-(3'-trifluoromethyl-4'-nitrophenyl)-4,4-dimethylimidazoline 2,5-dione for obtaining a medicament intended for the treatment of cancer affecting the following organs: bladder, brain, breast, lymphatic system, kidney, liver, skin and ovaries.

Even more particularly, a subject of the present patent application concerns the application of 1-(3'-trifluoromethyl)-4'-nitrophenyl)-4,4-dimethylimidazoline 2,5-dione in the treatment of breast, cancer, brain cancer, skin cancer and cancer of the ovaries, as well as the use of 1-(3-'trifluoromethyl 4'-nitrophenyl)-4,4-dimethylimidazoline 2,5-dione for obtaining a medicament intended for the treatment of breast cancer, brain cancer, skin cancer and cancer of the ovaries.

Finally, the present application concerns more particularly the application of 1-(3'-trifluoromethyl-4'-nitrophenyl)-4,4-dimethylimidazoline 2,5-dione in the treatment of breast cancer or cancer of the ovaries, as well as the use of 1-(3'-trifluoromethyl-4'-nitrophenyl)-4, 4-dimethylimidazoline 2,5-dione for obtaining a medicament intended for the treatment of breast cancer, or cancer of the ovaries.

In the application and the use described above, the medicaments containing, as active principle, 1-(3'-trifluoromethyl-4'-nitrophenyl)-4, 4-dimethylimidazoline 2,5-dione are administered by parenteral, oral, perlingual or rectal route. The preferred route is the oral or percutaneous route.

The medicaments used can be presented in the form of injectable suspensions, tablets, coated tablets, capsules, suppositories, and skin preparations. These medicaments are prepared in the standard way.

The doses used are variable according to the affection to be treated.

They can for example vary from 0.5 to 20 mg/kg per day by oral route. Preferably, the dose used varies from 1 to 5 mg/kg per day.

The activity of 1-(3'-trifluoromethyl-4'-nitrophenyl)-4,4-dimethylimidazoline 2,5-dione has been determined by measuring its anti-proliferative activity on the growth of mammary tumor cells MCF-7 and T 47-D.

DESCRIPTION OF THE TEST a) Cellular culture

The lines MCF-7 and T 47-D are kept in culture in an SVF (1) medium at 37° C. in a humid atmosphere containing 5% $CO_2$. The cells at subconfluence are gathered by trypsination (trypsine 0.05%, EDTA 0.02%) then rinsed by gentle centrifuging. A sample of cells in suspension is counted on a Malassez cell.

b) Study of growth

The cells resuspended in an SVF medium are sown a rate of 30,000 cells per tank in multi-tank plates (24 tanks of 2.5 cm ). Twenty four hours after the sowing (DO), the product under test is added to the medium in an ethanol solution (final concentration of ethanol: 0.1%) at a concentration of $10^{-5}M$, the control tanks receiving the same concentration of ethanol. The media are renewed every 48 hours. At the end of the experiment (D6 for the MCF-7 cells and D12 for the T 47-D cells), the medium is drawn off and the cells are immediately fixed by 150 microliters of methanol in order to measure the DNA.

The anti-proliferative activity of the products is evaluated by their capacity to inhibit the increase of DNA.

c) Measurement of DNA

The DNA is measured by a fluorimetric method using DABA (3,5-diamino-benzoic acid) (2) 150 microliters of DABA are added to each tank; the plates are then incubated for 45 minutes at 56° C., then 1.5 ml of IN HCl is added. The fluorescence is measured by fluorimetry (exciting wavelength: 400 nm, wavelength of emission: 500 nm). The quantity of DNA per tank is evaluated in relation to a standard range obtained by treating, under the same conditions, a standard DNA of a calf's thymus gland.

Results:

At a concentration of $10^{-5}M$, 1-(3'-trifluoromethyl-4'-nitrophenyl)-4, 4-dimethylimidazoline 2,5-dione inhibits the growth of MCF-7 and T 47-D cells by 30%.

(1) The culture medium of the foetal calf serum (FCS) is prepared as follows:

MEM medium (Minimal Essential Medium) to which are added: non-essential amino acids (GIBCO);
peni-strepto (penicillin 1000/ml, streptomycin 0.1 mg/ml); fungizone 0.1%;
insulin (5 ng/ml);
foetal calf serum (4% final concentration), 2) Puzas and Goodman, Analytical Biochemistry, Vol. 86, pp. 50-50, 1978.

Various modifications of the method of the invention may be made without departing from the spirit or scope thereof and it should be understood that the invention is intended to be limited only as defined in the appended claims.

What we claim is:

1. A method of treating hormone-dependent cancer of an organ selected from the group consisting of bladder, brain, breast, lymphatic systems, kidney, liver, skin and ovaries in warmblooded animal having such a cancer sensitive to treatment with 1-(3'-trifluoromethyl-4¹-nitro-phenyl)-4,4-dimethyl-imidazoline 2,5-dione comprising administering to said warm-blooded animal an amount of 1-(3'-trifluoromethyl-4'-nitro-phenyl)-4,4-dimethyl-imidazoline 2,5-dione sufficient to combat said hormone-dependent cancer.

2. The method of claim 1 wherein the cancer affects an organ selected from the group consisting of breast, brain, skin and ovaries.

3. The method of claim 2 wherein the organ is the breast or ovaries.

* * * * *